(12) United States Patent
Baker

(10) Patent No.: US 6,276,800 B1
(45) Date of Patent: Aug. 21, 2001

(54) SYSTEM FOR MODELING A WAVEFRONT USING SHEARED PHASE SHIFTS

(75) Inventor: Phillip C. Baker, Walnut Grove, CA (US)

(73) Assignee: Eyetech Vision, Inc., La Jolla, CA (US)

( * ) Notice: Subject to any disclaimer, the term of this patent is extended or adjusted under 35 U.S.C. 154(b) by 0 days.

(21) Appl. No.: 09/721,038

(22) Filed: Nov. 24, 2000

(51) Int. Cl.⁷ .................................................. A61B 3/10
(52) U.S. Cl. .............................................................. 351/211
(58) Field of Search .................................. 351/211, 212, 351/221, 246; 356/512, 515; 606/4, 5, 10, 11, 12

(56) References Cited

U.S. PATENT DOCUMENTS

| | | |
|---|---|---|
| 4,772,115 | 9/1988 | Gersten . |
| 5,307,097 | 4/1994 | Baker . |
| 5,909,270 | * 12/1999 | Moser et al. ........................ 351/212 |
| 6,002,484 | * 12/1999 | Rozema et al. ..................... 356/515 |

* cited by examiner

*Primary Examiner*—George Manuel
(74) *Attorney, Agent, or Firm*—Nydegger & Associates

(57) ABSTRACT

A device for imaging a wavefront to determine the optical properties of an eye includes a light source for directing an input light beam into the eye. Corrective optics focus this input beam onto a substantially circular area on the retina for reflection back through the eye as a return light beam from a point source. A shearing plate is used to introduce a phase disturbance into the return light beam and it includes at least one pattern that is positioned to determine phase shifts from the phase disturbance that was introduced into the return light beam. A computer is then used to create the wavefront image from these phase shifts.

20 Claims, 2 Drawing Sheets

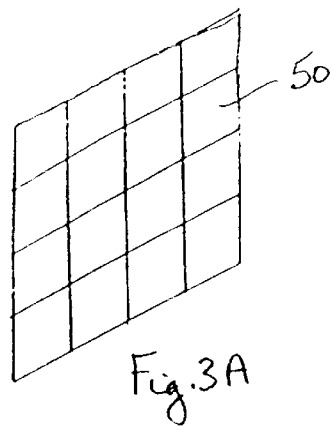
Fig. 3A
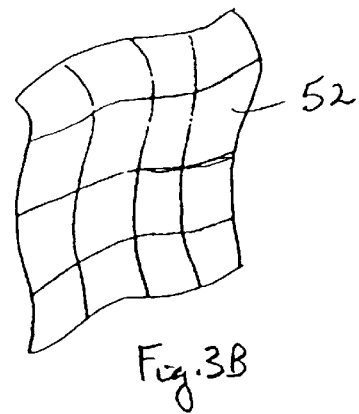
Fig. 3B
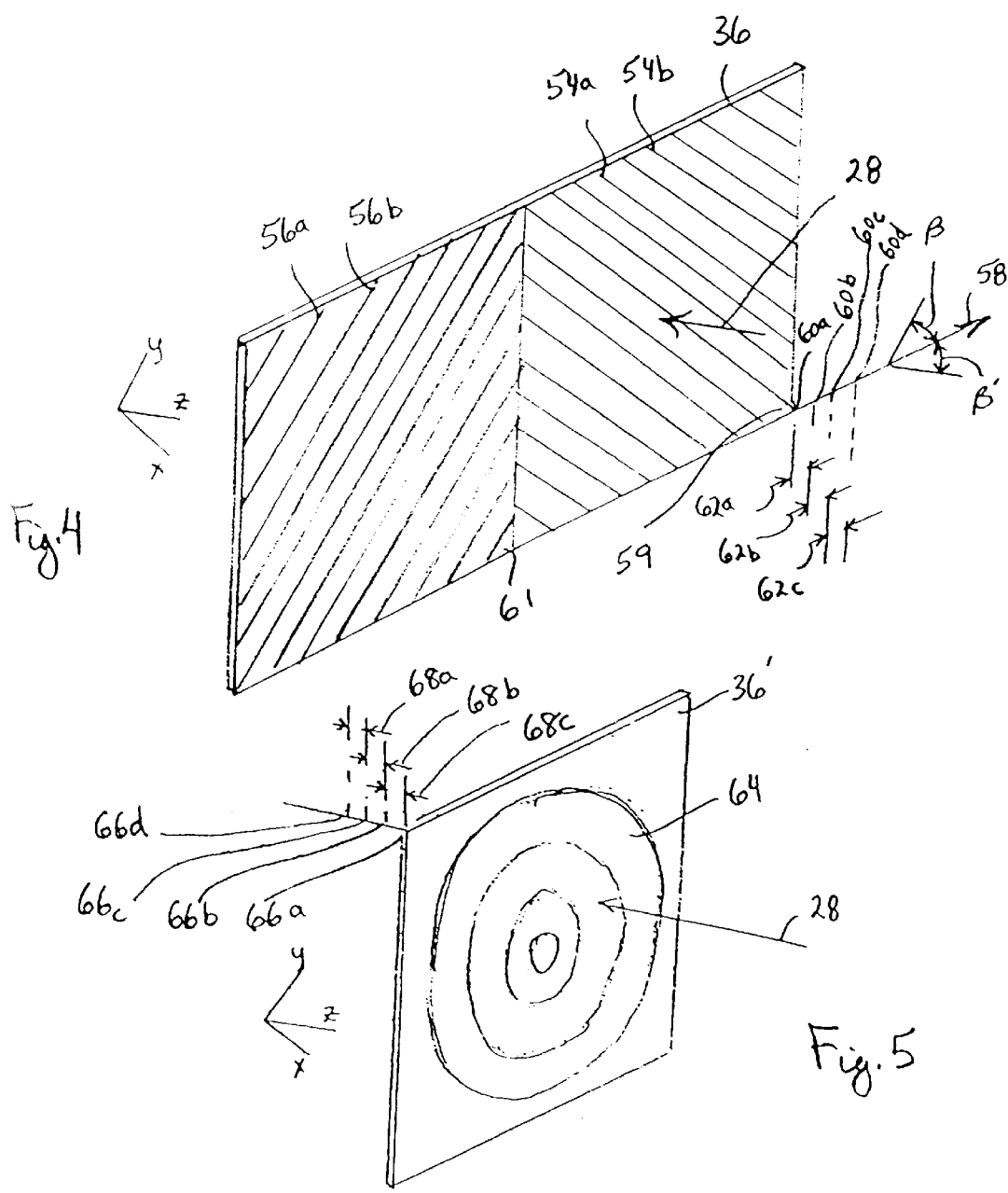
Fig. 4
Fig. 5

SYSTEM FOR MODELING A WAVEFRONT USING SHEARED PHASE SHIFTS

FIELD OF THE INVENTION

The present invention pertains generally to optical diagnostic equipment. More particularly, the present invention pertains to devices and methods that create wavefront images based on phase shifts between discrete rays of light in a light beam. The present invention is particularly, but not exclusively, useful for devices and methods that use wavefront analyses to detect optical aberrations of the eye.

BACKGROUND OF THE INVENTION

By definition, light is electromagnetic radiation that is capable of inducing a visual sensation in the eye. Under this definition, it is common to describe light as being sinusoidal in nature, and as having wavelengths in a range between about four hundred and eight hundred nanometers (400–800 nm). When light travels as a sinusoidal wave, it will travel through a distance of one wavelength during each of its cycles. Mathematically, these cycles can be expressed as angles where one complete cycle for the sinusoidal wave corresponds to $2\pi$ radians or 360°.

In order to compare different beams of radiation to each other, when both beams have the same wavelength, it is sometimes helpful to identify the phase difference or phase shift between the beams. For this purpose, phase can be defined as the fraction of a periodic waveform that has been completed at a specific reference time. Thus, if a first ray of light and a second ray of light have the same wavelength, $\lambda$, and they travel from the same start point through the same medium, but they start at different times, the difference in their respective start times can be expressed as a phase shift. The same argument, of course, applies for their arrival at a common distance from the start point. Thus, for example, if the second ray of light starts one half of a wavelength behind the first ray of light, the phase shift between the first ray of light and the second ray of light will be $\pi$ radians, or 180°. Due to this phase shift, the first ray of light will arrive at a common destination one half of a wavelength ahead of the second ray of light.

With the above in mind, it is to be appreciated that a beam of light can be considered as being composed of many individual rays of light. Further, though these rays of light may have the same wavelength, at a particular point in space each light ray will have its own characteristic phase that may, or may not, be the same as the phases of the other light rays. Building on this notion, it is to be appreciated that as a beam of light passes at angles through different media, individual rays in the beam will be refracted through different distances. The consequence then is that the different rays of light in the beam will be affected differently. Stated differently, as individual rays of light in the beam travel along paths of different lengths, there will be a phase shift between the rays. This happens, for example, as a beam of light passes through the optical components of an eye (e.g. lens, cornea). One technique for determining the extent of these differences, and their consequences for diagnostic purposes, is known as wavefront analysis.

In one aspect of a wavefront analysis, the individual rays in a light beam are evaluated for their respective phase. Specifically, this is be done as they pass through a common plane. In this case, if all rays in the beam that have the same wavelength, also have exactly the same phase as they pass through this common plane, a plane wavefront results. On the other hand, if the rays in the beam have different phases, the wavefront will be distorted. Depending on the extent, position and nature of the distortions in the wavefront, the optical characteristics of the path traveled by individual light rays in the beam can be analyzed.

With the above in mind, consider an eye. If light can be radiated from a point source on the retina of the eye, this light will initially radiate as a light beam having a plane wavefront. As the beam travels outwardly through the eye, however, it will pass through optical components of the eye which may, or may not, introduce aberrations into the light beam. In turn, these aberrations will manifest themselves as distortions of the wavefront.

Consequently, by determining the wavefront of a light beam, after it has passed through an eye, it is possible to evaluate the wavefront and to determine therefrom whether the aberrations that have been introduced are normal or require corrective action.

In light of the above, it is an object of the present invention to provide a device for imaging a wavefront for evaluating the optical properties of an eye. Another object of the present invention is to provide a device which generates wavefront data based on the phase shifts in a light beam that are caused when light passes through an eye. It is another object of the present invention to provide a device for imaging a wavefront which effectively establishes a point source of light on the retina of the eye. Still another object of the present invention is to provide a device for imaging a wavefront to evaluate the optical properties of an eye that is easy to use, relatively simple to manufacture, and comparatively cost effective.

SUMMARY OF THE PREFERRED EMBODIMENTS

A device for imaging a wavefront to determine the optical properties of an eye includes a light source that is used for directing an input light beam into the eye. More specifically, the input light beam is focused onto a substantially circular area on the retina. This effectively establishes a point source of light on the retina. Light from this point source is then reflected as scattered light back through the eye along a return light beam path. For purposes of the present invention, the input beam is preferably oriented at an angle to the return beam so that the two beams are not coincident. Also, the angle between the input beam and the return beam is preferably in a range from approximately five tenths of a degree to approximately twenty degrees (0.5°–20°).

An optical means, such as focusing lenses and mirrors that are well known in the art, is used to direct the return light beam along a beam path toward a shearing plate. As intended for the present invention, this shearing plate will preferably have one of two different configurations. One of these configurations is useful for effecting a lateral shear of the return light beam while the other is useful for effecting a radial shear of the return light beam.

In the configuration for the shearing plate that is effective for introducing a lateral shearing of the return light beam, the shearing plate includes two substantially coplanar patterns that are superposed and oriented so that phase shifts are taken in a plane substantially perpendicular to the return beam path. For reference purposes, consider that the return beam path is oriented in a z-direction and that the patterns lie in an x-y plane perpendicular to the z-direction. Within this reference system, the superposed patterns are positioned so that one pattern introduces a phase disturbance into the return light beam in one predetermined direction (e.g. the x-direction), while the other pattern introduces a phase disturbance into the return light beam in a substantially perpendicular direction (e.g. the y-direction). From these phase disturbances, phase shifts in the return light beam can be measured in both the x and y directions. In an alternate configuration for the shearing plate (radial shear), a single pattern can be used which will introduce a phase disturbance into the return light beam in the z-direction, i.e. along the beam path of the return light beam. Phase shifts in the return light beam can then be measured from the phase disturbance in the z-direction.

Although the input beam for the device of the present invention may be white light (i.e. includes all visible wavelengths for light), the input beam preferably includes wavelengths that are in a range from approximately seven hundred and twenty microns to approximately nine hundred microns. On the other hand, the patterns that are to be used to determine phase shifts in the return beam are responsive to only a specific wavelength. In the case of the configuration for a lateral shearing plate, both patterns are responsive to the same specific wavelength.

The device of the present invention also includes a motor for moving the pair of shearing plates in successive stepped increments in the path of the return beam. Specifically, each of these increments is equal to a distance that is substantially one quarter of the wavelength of the light that is being measured by the patterns in the shearing plate. In the case of the lateral shearing plate, the plate is moved in a direction that is forty five degrees from both the x-direction and the y-direction. Thus, by virtue of their respective orientations, the two patterns in the lateral shearing plate can simultaneously determine phase shifts in the return beam in orthogonal directions (i.e. the x and y directions). In the case of the radial shearing plate, the plate will be moved in increments along the beam path in the z-direction. For both configurations of the shearing plate, by virtue of the movements through successive stepped increments, the respective patterns are able to determine a figuration for the highs and the lows of the sinusoidal fluctuations in the light of the return beam. A computer is then employed to use the phase shift information that is generated from the phase disturbances introduced by the shearing plates, and to use the figuration of the phase shifts, to create an image of the wavefront of the return beam. This wavefront can then be subsequently analyzed to determine optical properties of the eye being examined.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 3A is an idealized representation of a plane wavefront;

FIG. 3B is an idealized representation of a distorted wavefront;

FIG. 4 is a perspective view of the shearing plate shown in FIG. 2 having superposed lateral shearing patterns; and FIG. 5 is a perspective view of the shearing plate shown in FIG. 2 having a radial shearing pattern.

DESCRIPTION OF THE PREFERRED EMBODIMENT

Figure 1:
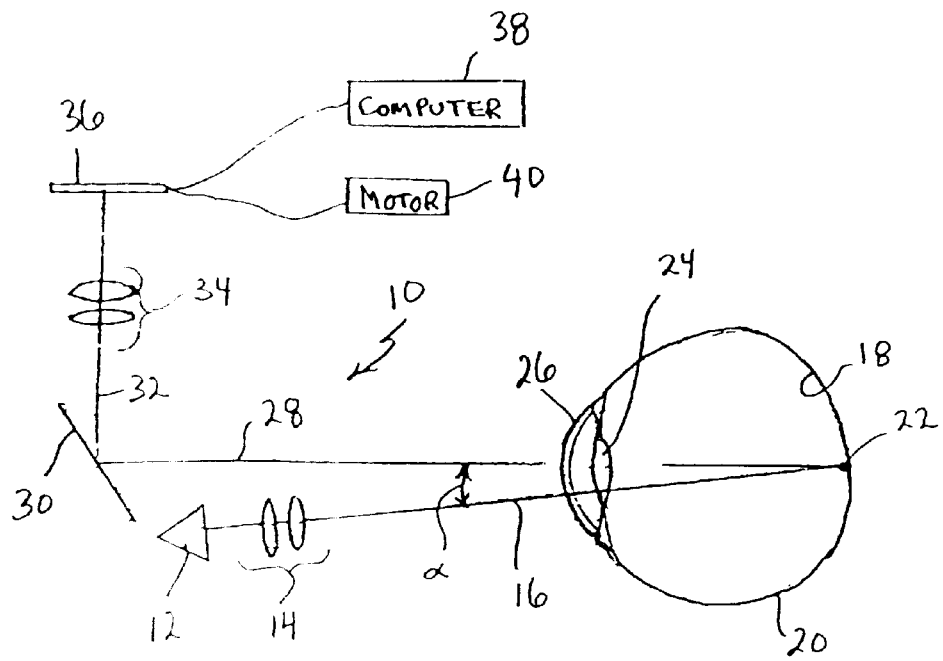
FIG. 1 is a schematic diagram of the device of the present invention shown in relation to an eye.

Referring initially to FIG. 1, a device for imaging a wavefront to determine the optical properties of an eye is shown and is generally designated 10. As shown, the device 10 includes a light source 12 positioned to radiate light through corrective optics 14 to generate an input light beam 16. For purposes of the present invention, the input light beam 16 can be white light but, preferably, it will include some light having wavelengths in a range from approximately seven hundred and twenty microns to approximately nine hundred microns. Specifically, the corrective optics 14 of the device 10 are arranged to focus the input light beam 16 onto the retina 18 of the eye 20. More specifically, the focal spot 22 on the retina 18 will be substantially circular. With this configuration, the focal spot 22 will generally function as a point source of light.

As intended for the present invention, scattered light from the focal spot 22 on the retina 18 of eye 20 will be directed back through the eye 20 through the lens 24 and cornea 26 of the eye 20. This light will then emerge from the eye 20 as a return beam of light 28. For purposes of the present invention, the return light beam 28 will not be coincident with the input light beam 16 and, instead, will be at an angle $\alpha$, to the input light beam 16. For the present invention, the angle $\alpha$, between the input light beam 16 and the return light beam 28 will be in a range between approximately five tenths of a degree and approximately twenty degrees.

Still referring to FIG. 1, it will be seen that after emerging from the eye 20 the return light beam 28 is directed by a turning mirror 30 along a beam path 32. Optical elements 34 on the beam path 32 can be used to specifically direct the return light beam 28 to a shearing plate 36. For the purposes of the present invention, the shearing plate 36 is electronically connected to a computer 38, and it is mechanically connected to a motor 40. In keeping with this disclosure for the device 10 of the present invention, the connections between the shearing plate 36, the computer 38 and the motor 40 can be accomplished in ways well known to the skilled artisan in the pertinent art.

Figure 2:
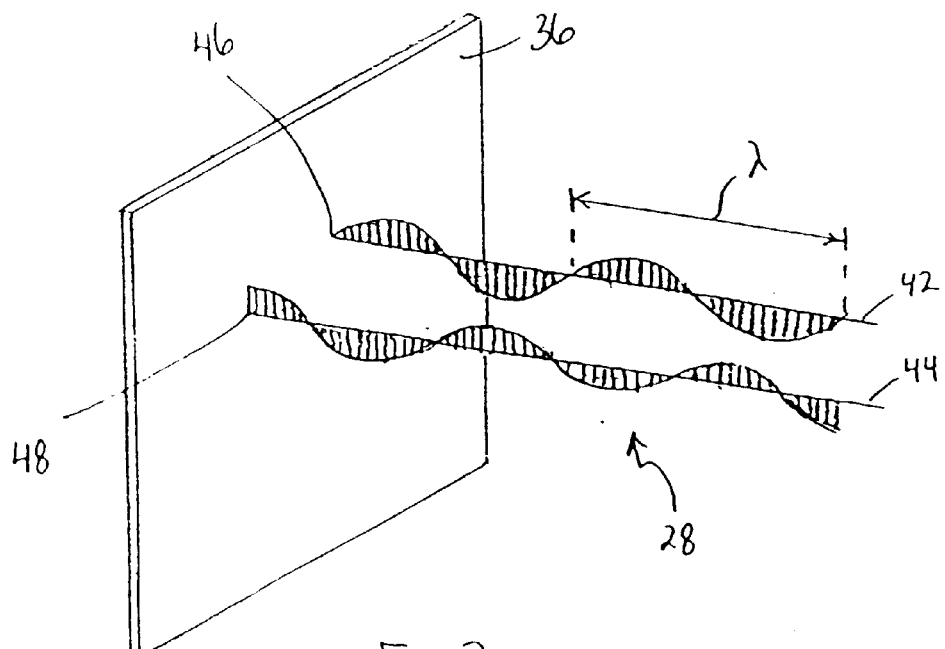
FIG. 2 is a perspective view of a shearing plate for use in the device of the present invention, the shearing plate being shown receiving two light rays of a light beam wherein both light rays have the same wavelength but different phases.

Referring now to FIG. 2, the phase shift phenomenon that leads to the construction of a wavefront is illustrated by considering two different rays of light in the return light beam 28. Specifically, a light ray 42 and a light ray 44 are shown being radiated as part of the return light beam 28 toward the shearing plate 36. Although only the light rays 42 and 44 are shown in FIG. 2, it is to be appreciated that the return light beam 28 is composed of many such light rays, and that the light rays 42 and 44 are only exemplary. Further, as shown in FIG. 2, the light rays 42 and 44 have the same wavelength $\lambda$, they are both directed substantially perpendicular to the shearing plate 36, and they are respectively incident on the shearing plate 36 at the points 46 and 48. The light rays 42 and 44, however, are shown out of phase with each other.

When comparing the two light rays 42 and 44 to each other, it is convenient to consider the phase of their respective cycles. In this case, a cycle is considered as being one wavelength ($\lambda$ of $2\pi$ radians, 360°) such as is shown for the light ray 42 in FIG. 2. Recall, the light rays 42 and 44 have the same wavelength $\lambda$. With this in mind, however, it is seen in FIG. 2 that the light ray 42 is shown incident at the point 46 on shearing plate 36 with a different phase than that of the light ray 44, when it is incident at the point 48. Specifically, for the case illustrated in FIG. 2, the light ray 44 can be considered as either being one quarter of a wavelength ahead of the light ray 42 or, alternatively, three quarters of a wavelength behind the light ray 42. With either perspective, the difference between the phase of the light ray 42 and the phase of the light ray 44 is known as a phase shift.

Although only the light rays 42 and 44 of return light beam 28 are shown in FIG. 2, as indicated above there will be many such light rays in the return light beam 28. Importantly, the phase shifts between any two light rays in the return light beam 28 can be described in the same manner as was done above for the light rays 42 and 44. The consequence of this is that the return light beam 28 can be effectively described by its wavefront. As is well known in the art, a wavefront is essentially a map of the phase differences between the individual light rays (e.g. light rays 42, 44) in a beam of light (e.g. return light beam 28).

Consider for the moment that all light rays in the return light beam 28 are the same as light ray 42. In this case, as the light rays of the return light beam 28 are incident on the shearing plate 36, they will all be in phase. The result in this case is a plane wavefront 50, such as is illustrated in FIG. 3A. On the other hand, when the different light rays in the return light beam 28 are out of phase with each other, the consequent phase shifts create a distorted wavefront 52, such as is illustrated in FIG. 3B. It happens, as shown for the present invention in FIG. 1, that as light passes through the lens 24 and cornea 26 of the eye 20, optical aberrations will be introduced into the light that are manifest as a distorted wavefront 52 in the return light beam 28. It is known that the location, magnitude, and relative relationship of the phase shifts that contribute to the distorted wavefront 52 in a return light beam 28 can be used for purposes of diagnosing the optical properties of the eye 20.

Turning now to FIG. 4, a shearing plate 36 for use in the device 10 is shown to include a diagonal pattern 54 which is juxtaposed with a cross diagonal pattern 56. Specifically, the diagonal pattern 54 (the pattern lines 54a and 54b are only exemplary) extends generally in the x-direction and the cross diagonal pattern 56 (the pattern lines 56a and 56b are also only exemplary) extends generally in the y-direction. Thus, the diagonal pattern 54 and the cross diagonal pattern 56 are substantially coplanar and are orthogonal to each other. In the operation of the device 10, the shearing plate 36 will be positioned or oriented so that the x-y plane of the shearing plate 36 will be substantially perpendicular to the beam path of the return light beam 28. Stated differently, the return light beam 28 will radiate toward the shearing plate 36 in the z direction.

For purposes of the present invention, both of the diagonal patterns 54 and 56 introduce phase disturbances into the return light beam 28. Importantly, phase shifts between the various light rays in the return light beam 28 can be measured from these phase disturbances. For example, the phase shift between a light ray incident at a point on pattern line 54a and a light ray incident at a point on pattern line 54b can be measured. Similarly, the phase shift between points on respective pattern lines 56a and 56b can be measured. When collectively considered for all of the various points on the shearing plate 36, a wavefront can be created, albeit incomplete. In order to determine a figuration for the sinusoidal waves that comprise the return light beam 28, it is necessary to determine where the phase shift is being measured within each cycle. Stated differently, it is necessary to know where the highs and lows of the cycles in respective light rays are located relative to each other. This can be done by sequentially measuring the phase shifts between all of the light rays in the return light beam 28 from successive quarter wavelength perspectives.

Still referring to FIG. 4 it will be appreciated that the motor 40 can be activated to move the shearing plate 36 in a direction 58 that is substantially perpendicular to the z direction and the beam path of the return light beam 28. More specifically, the direction 58 is chosen such that the angle β, between the direction 58 and the y direction is substantially equal to the angle β', between the direction 58 and the x direction, i.e. angle β, is equal to angle β', is equal to forty five degrees. This is done so that movement of the shearing plate 36 in the direction 58 will effectively move the diagonal pattern 54 and the cross diagonal pattern 56 of shearing plate 36 through a same distance in the direction 58.

In order to generate a wavefront image with a lateral shear, by using the shearing plate 36 shown in FIG. 4, an image of the return light beam 28 is taken with the corner 59 of diagonal pattern 54 of shearing plate 36 in the location 60a. The motor 40 is then activated to move the diagonal pattern 54 through an increment 62a in the x-direction to the location 60b. For the purposes of the present invention the increment 62a is equal to one quarter wavelength ($\lambda/4$). As will be appreciated by the skilled artisan, the result is that all phase shifts in the x-y plane are then measured from a perspective (location 60b) that is one quarter wavelength different from the previous measurement (location 60a). Subsequently, additional phase shift measurements can be taken at locations 60c and 60d after motor 40 has moved the diagonal pattern 54 through respective increments 62b and 62c. The process is then repeated for the diagonal pattern 56. Specifically, the corner 61 of cross diagonal pattern 56 is positioned at the location 60a and the cross diagonal pattern 56 is then incrementally moved through the increments 62a–c. As intended for the present invention, all phase shift measurements for both diagonal pattern 54 and cross diagonal pattern 56 (locations 60a–d) are compiled, evaluated and collated to create an image of the distorted wavefront 52. As indicated above, the resultant distorted wavefront 52 can then be used for diagnostic purposes.

In an alternate embodiment for the present invention, a shearing plate 36' is shown in FIG. 5. Unlike the shearing plate 36, which created a lateral shear of the return light beam 28, the shearing plate 36' creates a radial shear. Specifically, the circular pattern 64 introduces a phase disturbance into the return light beam 28 which is indicative of phase shifts measured in the z direction. Again, like shearing plate 36, the shearing plate 36' is moved through a sequence of locations 66 through successive one quarter wavelength increments 68. This time, however, the increments 68 are taken in the z direction. Accordingly, starting at the location 66a, phase shifts across the x-y plane can be measured by the pattern 64. Motor 40 then moves the shearing plate 36 through an increment 68a to the location 66b where phase shifts having a one quarter wavelength change in perspective are again measured by the circular pattern 64. This continues through increments 68b and 68c to respective locations 66c and 66d. As with shearing plate 36, these movements allow the shearing plate 36' to determine a figuration for the sinusoidal waves of the return light beam 28. Also, as with the shearing plate 36, the various phase shift measurements that are taken using the shearing plate 36' are used by the computer 38 to create a wavefront image for the return light beam 28. Similarly, the resultant distorted wavefront 52 of the return light beam 28 can be used for diagnostic purposes.

While the particular System for Modeling a Wavefront Using Sheared Phase Shifts as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A device for imaging a wavefront characteristic of the optical properties of an eye which comprises:
    a light source for directing an input light beam into the eye for reflection from the retina of the eye;
    an optical means for directing a return light beam along a beam path, wherein light in said return light beam is scattered light reflected from the retina;
    a shearing plate having at least one pattern for introducing a phase disturbance into said return light beam, said pattern having an orientation for determining phase shifts in said return light beam, said phase shifts being measured from said phase disturbance in a predetermined direction; and
    a computer means for using said phase shifts to create said image of said wavefront.

2. A device as recited in claim 1 comprising a pair of said patterns in said shearing plate wherein said patterns are superposed with said direction of one said pattern being substantially perpendicular to said direction of said other pattern in a plane.

3. A device as recited in claim 2 wherein each of said pair of patterns in said shearing plate measure respective lateral shears in said plane substantially perpendicular to said beam path.

4. A device as recited in claim 3 further comprising motor means for moving said shearing plate through successive increments to determine a figuration for said phase shifts, and wherein each said increment is a distance equal to substantially one quarter wavelength.

5. A device as recited in claim 1 wherein said pattern is responsive to a wavelength in a range from approximately seven hundred and twenty microns to approximately nine hundred microns.

6. A device as recited in claim 1 wherein said pattern measures a radial shear with said predetermined direction being aligned along said beam path.

7. A device as recited in claim 1 further comprising corrective optics for focusing said input beam onto a substantially circular area on the retina.

8. A device as recited in claim 1 wherein said input beam is oriented at an angle to said return beam.

9. A device as recited in claim 8 wherein said angle is in a range from approximately five tenths of a degree to approximately twenty degrees.

10. A device as recited in claim 1 wherein light from said light source is white light.

11. A device for imaging a wavefront characteristic of the optical properties of an eye which comprises:
    an optical means for focusing an input light beam onto a substantially circular area on the retina of the eye to generate a return light beam, said return beam containing scattered light reflected from said circular area and out of the eye along a beam path;
    a means for introducing a phase disturbance into said return light beam to determine phase shifts therein, wherein said phase shifts are measured from said phase disturbance in a predetermined direction; and
    a computer means for using said phase shifts to create said image of said wavefront.

12. A device as recited in claim 11 wherein said phase disturbance introducing means comprises a shearing plate having a pair of superposed patterns, wherein said patterns are oriented in a plane with said predetermined direction for one said pattern being substantially perpendicular to said predetermined direction for said other pattern to measure respective lateral shears in said plane substantially perpendicular to said beam path.

13. A device as recited in claim 12 wherein said pair of patterns are responsive to a same wavelength in a range from approximately seven hundred and twenty microns to approximately nine hundred microns, and wherein said device further comprises a motor means for moving said shearing plate through successive increments to determine a figuration for said phase shifts, with each said increment being a distance equal to substantially one quarter wavelength.

14. A device as recited in claim 11 wherein said optical means comprises:
    a light source for generating said input light beam; and
    corrective optics for focusing said input beam onto said substantially circular area on the retina.

15. A device as recited in claim 11 wherein said input light beam is white light and wherein said input light beam is oriented at an angle to said return beam, and said angle is in a range from approximately five tenths of a degree to approximately twenty degrees.

16. A device as recited in claim 11 wherein said pattern measures a radial shear with said predetermined direction being aligned along said beam path.

17. A method for imaging a wavefront characteristic of the optical properties of an eye which comprises the steps of:
    focusing an input light beam into the eye for reflection from the retina and out of the eye as a return light beam, wherein light in said return light beam is scattered light reflected from the retina;
    directing said return light beam along a beam path;
    positioning at least one pattern on said beam path to introduce a phase disturbance into said return light beam, said pattern having an orientation for measuring phase shifts in said return light beam, said phase shifts being measured from said phase disturbance in a predetermined direction;
    moving said pattern through successive increments to determine a figuration said phase shifts wherein each said increment is a distance equal to substantially one quarter wavelength; and
    using said phase shifts to create said image of said wavefront.

18. A method as recited in claim 17 wherein said positioning step is accomplished using a pair of said patterns, wherein said patterns substantially coplanar and are superposed with said predetermined direction of one said pattern being substantially perpendicular to said predetermined direction of said other pattern, and wherein each of said pair of patterns is responsive to a same wavelength and said wavelength is in a range from approximately seven hundred and twenty microns to approximately nine hundred microns.

19. A method as recited in claim 17 wherein said focusing step is accomplished with corrective optics for focusing said input beam onto a substantially circular area on the retina and wherein said input beam is oriented at an angle to said return beam and said angle is in a range from approximately five tenths of a degree to approximately twenty degrees.

20. A method as recited in claim 17 wherein said pattern measures a radial shear with said predetermined direction being aligned along said beam path.

* * * * *